United States Patent [19]

Neustadt et al.

[11] 4,272,550
[45] Jun. 9, 1981

[54] OMEGA-[4-(POLYFLUORO-2-HYDROXY-2-PROPYL)-2,3,6-SUBSTITUTED-PHENOXY AND PHENYLTHIO]ALKANOIC ACIDS AND COMPOUNDS RELATED THERETO

[75] Inventors: Bernard R. Neustadt; Elijah H. Gold, both of West Orange, N.J.

[73] Assignee: Schering Corporation, Kenilworth, N.J.

[21] Appl. No.: 89,804

[22] Filed: Oct. 31, 1979

Related U.S. Application Data

[62] Division of Ser. No. 35,963, May 4, 1979, Pat. No. 4,199,597.

[51] Int. Cl.$^3$ ............... A61K 31/135; A61K 31/165; C07C 93/06; C07C 103/26
[52] U.S. Cl. ............................... 424/324; 260/343.7; 260/465 E; 260/465 F; 260/465 G; 260/501.1; 260/501.17; 260/501.19; 424/330; 560/49; 564/162; 564/164; 564/165; 564/175; 564/341; 564/353; 564/354; 564/134

[58] Field of Search ............... 424/324, 330; 260/559 T, 558 S, 559 A, 559 B, 570.5 S, 570.7; 564/162, 164, 165, 175, 341, 353, 354

[56] References Cited

U.S. PATENT DOCUMENTS

| | | | |
|---|---|---|---|
| 3,927,092 | 12/1975 | Bolhofer | 260/559 B |
| 4,117,166 | 9/1978 | Baker et al. | 424/324 |
| 4,119,433 | 10/1978 | Baker et al. | 71/118 |
| 4,148,923 | 4/1979 | Giudicelli et al. | 424/330 |
| 4,199,597 | 4/1980 | Neustadt et al. | 560/11 |

Primary Examiner—G. T. Breitenstein
Attorney, Agent, or Firm—Barbara L. Renda; Mary S. King

[57] ABSTRACT

Omega-[4-(polyfluoro-2-hydroxy-2-propyl)-2,3,6-substituted-phenoxy and phenylthio]alkanoic acids and compounds related thereto having antihypertensive activity are preparable by reaction of the appropriate 2,3,6-substituted-4-(polyfluoro-2-hydroxy-2-propyl)-phenol or thiophenol with an alkyl ester of a bromoalkanoic acid, followed by hydrolysis to the free acid.

6 Claims, No Drawings

OMEGA-[4-(POLYFLUORO-2-HYDROXY-2-PROPYL)-2,3,6-SUBSTITUTED-PHENOXY AND PHENYLTHIO]ALKANOIC ACIDS AND COMPOUNDS RELATED THERETO

This is a division of application Ser. No. 35,963, filed May 4, 1979, now U.S. Pat. No. 4,199,597.

The present invention relates to omega-[4-(polyfluoro-2-hydroxy-2-propyl)-2,3,6-substituted-phenoxy and phenylthio]-alkanoic acids and compounds related thereto. More particularly, this invention relates to compounds of the general formula

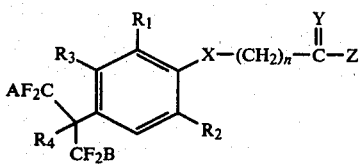

wherein A and B are independently hydrogen, chloro or fluoro, $R_1$ is hydrogen, halo, lower alkyl or lower alkoxy;
$R_2$ is halo, lower alkyl or lower alkoxy;
$R_3$ is hydrogen or lower alkyl;
$R_4$ is hydroxy, lower alkoxy, amino, or mono- or di-lower alkyl amino;
n is 1–4;
X is oxygen or $S(O)_m$ wherein m is 0–2;
Y is oxygen or (H,H); and
Z is hydroxy, lower alkoxy, amino, mono- or di-lower alkylamino or mono- or di-aralkylamino when Y is oxygen; or amino, mono- or di-lower alkylamino or aralkylamino which Y is (H,H); and the pharmaceutically acceptable salts thereof.

The lower alkyl groups referred to above preferably contain 1–6 carbon atoms and include methyl, ethyl, propyl, butyl, pentyl, hexyl and the corresponding branched chain isomers thereof. The lower alkoxy groups likewise contain 1–6, and preferably 1–3, carbon atoms and are illustrated by methoxy, ethoxy, n-propoxy, isopropoxy and the like. The aryl groups encompassed by the above formula are those containing 6–10 carbon atoms, such as phenyl and lower alkyl substituted-phenyl, e.g., tolyl and xylyl, and phenyl substituted by 1–2 halo, hydroxy or lower alkoxy groups.

The halo atoms in the above formula may be fluoro, chloro, bromo or iodo.

For the purposes of this invention, equivalent to the compounds of formula (I) wherein Y is (H,H) and Z is amino, mono- or di-lower alkylamino or mono- or di-aralkylamino, are the pharmaceutically acceptable acid addition salts thereof. Such acid addition salts may be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids. Similarly, with the compounds of formula I wherein Y is oxygen and Z is hydroxy amine salts can be formed with a variety of amines such as procaine or N,N'-dibenzylethylenediamine.

Additionally, the compounds of formula (I) wherein Y is oxygen and Z is hydroxy are capable of forming alkali metal and alkaline earth metal cationic salts when reacted with equimolar quantities of the appropriate base. For instance, treatment of 2-[4-(hexafluoro-2-hydroxy-2-propyl)-2-methoxy-6-methylphenoxy]-acetic acid with sodium hydroxide affords sodium 2-[4-(hexafluoro-2-hydroxy-2-propyl)-2-methoxy-6-methylphenoxy]acetate. Similarly, the appropriate quantity of potassium or calcium hydroxide affords the potassium or calcium salt.

Preferred compounds of this invention are those wherein X is oxygen, and particularly those wherein Y is hydroxy. Of these, especially preferred are those wherein $R_1$ and $R_2$ are both methyl or isopropyl or where $R_1$ is methyl and $R_2$ is methoxy.

The compounds of this invention are useful in view of their pharmacological properties. In particular, they possess activity as antihypertensive agents as evidenced by their ability to reduce blood pressure in animals in which the blood pressure has become abnormally elevated.

The antihypertensive activity of the instant compounds is demonstrated by the results of a standardized test for such activity using male, spontaneously hypertensive rats in which systolic blood pressures and heart rates are recorded by the semi-automated indirect procedure of Vaynofsky. Among the compounds of this invention which have been found particularly active in this test are the representative compounds 2-[4-(hexafluoro-2-hydroxy-2-propyl)-2,6-dimethylphenoxy]acetic acid; 2-[4-(hexafluoro-2-hydroxy-2-propyl)-2-methyl-6-methoxyphenoxy]acetic acid; 2-[4-(hexafluoro-2-methoxy-2-propyl)-2,6-dimethylphenoxy]acetic acid; and ethyl 2-[4-(hexafluoro-2-hydroxy-2-propyl)2,6-diisopropylphenoxy]acetate. Other compounds found active in this test procedure include 2-[2,6-dimethyl-4-(hexafluoro-2-hydroxy-2-propyl)-phenoxy]ethylamine and N-benzyl-2-[4-(hexafluoro-2-hydroxy-2-propyl)-2,6-dimethylphenoxy]acetamide.

In view of their potent pharmacological properties, the compounds of this invention can be combined with pharmaceutical carriers and administered in a variety of well-known pharmaceutical forms suitable for oral or parenteral administration to provide compositions useful in the treatment of cardiovascular disorders and particularly, mammalian hypertension.

Based upon laboratory tests, the effective dose ($ED_{50}$) of the compounds of this invention will typically be in the range of about 0.5 to about 100 mg/kg, preferably about 1–10 mg/kg, of mammalian weight administered in single or divided doses. The exact dose to be administered is dependent upon where the particular compound lies within the above quoted range, as well as upon the age, weight and condition of the individual.

The composition containing the compounds of this invention will preferably contain from about 5 to about 250 mg. of the active compound per dosage unit. They are most preferably administered orally. Typical formulations for oral administration are those such as tablets, capsules, syrups, elixirs or suspensions. Typical injectable formulations include solutions and suspensions.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate, sodium sulfate; calcium sulfate; polyvinylpyrrolidone; polyvinyl alcohol; stearic acid; alkaline earth metal stearates such as magnesium stearate and calcium stearate; stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids: as well as other non-toxic compatible fillers, binders, disintegrants and lubricants commonly used in pharmaceutical formulations.

In treating certain patients with the compounds of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide, may be added.

The compounds of formula (I) wherein $R_4$ is hydroxy, amino or mono- or di-lower alkylamino, Y is oxygen and Z is lower alkoxy may be conveniently prepared by contacting the appropriate 2,6-disubstituted-4-(polyfluoro-2-hydroxy-2-propyl)phenol or thiophenol of the formula

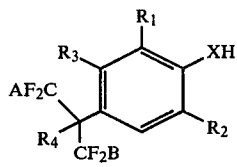

(II)

wherein X, A, B, $R_1$, $R_2$ and $R_3$ are as hereinbefore defined except that m cannot be 1 or 2, and $R_4$ is hydroxy, amino, or mono- or dilower alkylamino with an appropriate bromoester of the formula

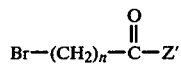

(III)

wherein n is as hereinbefore defined and Z' is lower alkoxy. The reaction is preferably conducted in the presence of an acid acceptor such as potassium carbonate. Depending on the nature of the particular reactants, a solvent may be used, and generally, the use of a solvent is preferred. Suitable solvents are those such as acetone, acetonitrile and dimethylformamide. Preferred reaction times are 2–20 hours. Elevated temperatures may be used, but room temperature is generally preferred.

The starting materials of formula (II) wherein X is oxygen, may be prepared by the methods of Gilbert and Litt, U.S. Pat. No. 3,324,185, Farah, et. al., *J. Org. Chem.*, 30 (4), 998–1001 (1965) and Sheppard, *J. Org., Chem.*, 33, 3297–3306 (1968). The starting materials of formula (II) wherein X is sulfur may be prepared by treatment of the corresponding aniline with nitrous acid and potassium ethyl xanthate to convert the amine to a thiophenol.

The compounds of formula (I) wherein $R_4$ is lower alkoxy, and Z is other than hydroxy may be prepared by contacting the compounds of formula (I) wherein $R_4$ is hydroxy, and Z is other than hydroxy with a strong base such as sodium hydride and adding an appropriate lower alkyl halide. The halide is preferably the iodide, but the bromides or chlorides may also be used. The reaction preferably is conducted in a polar, aprotic solvent such as dimethylformamide or dimethyl sulfoxide. The compounds wherein $R_4$ is lower alkoxy and Z is hydroxy are prepared by hydrolysis of the corresponding compound wherein $R_4$ is lower alkoxy and Z is lower alkoxy as described hereinafter.

The compounds of formula (I) wherein Y is oxygen and Z is hydroxy may be prepared by hydrolysis of the corresponding compound wherein Y is oxygen and Z is lower alkoxy. This is most preferably accomplished using a strong base such as sodium or potassium hydroxide.

Compounds of formula (I) wherein Y is oxygen and Z is mono- or di-lower alkylamino or mono- or di-lower aralkylamino may be prepared by reaction of the compounds wherein Y is oxygen and Z is lower alkoxy with the appropriate mono- or di-lower alkylamine or mono- or di-lower aralkylamine. The reaction may be conducted in the presence or absence of a solvent depending upon the nature of the reactants. Generally, heating of the reactants to about 60°–120° C. facilitates the reaction.

Treatment of the compounds of formula (I) wherein Y is oxygen and Z is mono- or di-lower alkylamino or mono- or di-lower aralkylamino with a reducing agent such as lithium aluminum hydride or sodium-bis-(2-methoxyethoxy)aluminum hydride affords the corresponding compounds wherein Y is (H,H) and Z is mono- or di-lower alkylamino or aralkylamino.

Compounds of formula (I) wherein Y is (H,H) and Z is amino and m is not 1 or 2 may be prepared by reaction of a phenol or thiophenol of the formula (II) with chloroacetonitrile in the presence of an acid acceptor such as potassium carbonate to afford the intermediate of the formula

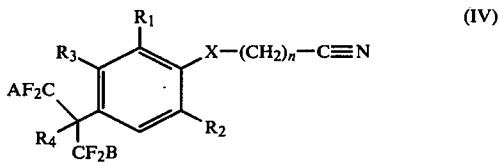

(IV)

wherein A, B, $R_1$, $R_2$, $R_3$, $R_4$, X and n are as hereinbefore defined except that m is not 1 or 2. The intermediate of formula (IV) may then be reduced utilizing a reducing agent such as borane in tetrahydrofuran or lithium aluminum hydride in ether to afford the desired compound of formula (I) wherein Y is two hydrogens and Z is amino. Oxidation of the intermediate IV as described hereinafter affords the compounds wherein m is 1 or 2. Alternatively, when X is not S or SO, catalytic hydrogenation may be used to accomplish the reduction.

The intermediate nitriles of formula (IV) are hydrolyzed to afford the compounds of formula (I) wherein Y is oxygen and Z is amino. Typically, sodium hydroxide is used, but acid hydrolysis with concentrated sulfuric acid or hydrochloric acid may also be utilized. In the case of certain sensitive nitriles, only a small amount of acid or base need be present to effect the transformation.

Compounds of formula I wherein X is $S(O)_m$ wherein m is 1 or 2 may be prepared from the corresponding compounds wherein m is 0 by oxidation with such reagents as hydrogen peroxide, m-chloroperbenzoic acid and the like.

The following examples describe in detail compounds illustrative of the present invention and methods which have been devised for their preparation. It will be apparent to those skilled in the art that many modifications, both of materials and methods, may be practiced without departing from the purpose and intent of this disclosure.

EXAMPLE 1

To 2,6-dimethyl-4-(hexafluoro-2-hydroxy-2-propyl)-phenol [Farah, et al, *J. Org. Chem.*, 30, 1003 (1965)], (10.0 g=35 mmol) in 100 ml acetonitrile add ethyl bromoacetate (6.9 g=42 mmol) and potassium carbonate (9.7 g=69 mmol). Stir 5 hours, filter and concentrate. Partition between ether and 1.0 N HCl. Dry and concentrate the ether extract. Recrystallize from ether-hexane to obtain, as white crystals, m.p. 99°-101° C., ethyl 2-[4-(hexafluoro-2-hydroxy-2-propyl)-2,6-dimethylphenoxy]acetate.

Repeating the procedure described above utilizing 2,6-diisopropyyl-4-(hexafluoro-2-hydroxy-2-propyl)-phenol affords ethyl 2-[4-(hexafluoro-2-hydroxy-2-propyl)-2,6-diisopropylphenoxy]-acetate, m.p. 91°-93° C.

Repetition of the procedure described in the first paragraph utilizing 2,6-dimethyl-4-(1,1,3,3-tetrafluoro-1,3-dichloro-2-hydroxy-2-propyl)phenol affords ethyl 2-[1,1,3,3-tetrafluoro-1,3-dichloro-2-hydroxy-2-propyl)-2,6-dimethylphenoxy]acetate.

Following the procedure described in the first paragraph using methyl bromoacetate in place of the ethyl bromoacetate yields methyl 2-[4-(hexafluoro-2-hydroxy-2-propyl)-2,6-dimethylphenoxy]acetate.

Substantial repetition of the procedure detailed in the first paragraph using ethyl 3-bromopropionate affords ethyl 3-[4-hexafluoro-2-hydroxy-2-propyl)-2,6-dimethylphenoxy]propionate.

EXAMPLE 2

To 2-methoxy-6-methylphenol (27.6 g=0.20 mol) in 300 ml toluene, add aluminum chloride (4.0 g=30 mmol). Bubble in hexafluoroacetone (47 g=0.28 mol) over 7 hours. Heat the reaction mixture in a steel bomb 16 hours at 120° C. Cool, and pour the contents onto 1.0 N HCl. Extract with ether. Wash the ether layer with 1.0 N NaOH. Acidify the basic aqueous layer with concentrated HCl, extract with ether, dry, concentrate and distill to obtain a fraction boiling at 71°-74° C./0.1 mm. Crystallize from cold hexane to obtain, as a solid, m.p. 44°-45° C., 4-(hexafluoro-2-hydroxy-2-propyl)-2-methoxy-6-methylphenol.

To the above phenol (6.0 g=20 mmol) in 100 ml acetonitrile add ethyl bromoacetate (3.0 g=24 mmol) and potassium carbonate (5.4 g=39 mmol). Stir 16 hours, filter, concentrate, and partition between ether and 1.0 N HCl. Dry and concentrate the ether. Partition between 1:1 ether-hexane and 1.0 N NaOH. Acidify the aqueous layer with concentrated HCl and extract with ether. Dry and concentrate. Recrystallize from ether-hexane and dry at 0.1 mm pressure to obtain 2-[4-(hexafluoro-2-hydroxy-2-propyl)-2-methoxy-6-methyl-phenoxy]acetic acid, m.p. 111°-113° C.

Utilization of 1,1,3,3-tetrafluoroacetone in the procedure detailed above in place of the hexafluoroacetone affords 2-[4-(1,1,3,3-tetrafluoro-2-hydroxy-2-propyl)-2-methoxy-6-methylphenoxy]acetic acid.

Following the above procedure of the first two paragraphs utilizing 2-ethoxy-6-ethylphenol, 2-isopropyl-phenol, or 2,6-dimethoxyphenol yields, respectively as products, 2-[4-(hexafluoro-2-hydroxy-2-propyl)-2-ethoxy-6-ethylphenoxy]acetic acid, 2-[4-(hexafluoro-2-hydroxy-2-propyl)-2-isopropylphenoxy]acetic acid and 2-[4-(hexafluoro-2-hydroxy-2-propyl)-2,6-dimethoxyphenoxy]acetic acid.

EXAMPLE 3

To ethyl 2-[4-(hexafluoro-2-hydroxy-2-propyl)-2,6-dimethylphenoxy]acetate (6.0 g=16 mmol) in 60 ml dry dimethylformamide add sodium hydride dispersion in mineral oil (0.85 g=18 mmol). Stir 1 hour and add methyl iodide (3.0 g=21 mmol). Let stir 2 hours and partition between water and ether. Wash the ether layer with water, dry and concentrate. Recrystallize from ether-hexane to obtain ethyl 2-[4-(hexafluoro-2-methoxy-2-propyl)-2,6-dimethylphenoxy]acetate, m.p. 97°-98° C.

Repeating the above procedure utilizing methyl 2-[4-hexafluoro-2-hydroxy-2-propyl)-2,6-dimethylphenoxy]acetate and ethyl iodide affords methyl 2-[4-(hexafluoro-2-ethoxy-2-propyl)-2,6-dimethylphenoxy]acetate.

EXAMPLE 4

Stir together for 16 hours a mixture of ethyl 2-[4-(hexafluoro-2-hydroxy-2-propyl)-2,6-dimethylphenoxy]acetate (7.1 g=19 mmol) and 125 ml 1.0 N NaOH. Acidify with concentrated HCl and extract with ether. Dry and concentrate the ether. Recrystallize from ether-hexane to obtain, as white crystals, 2-[4-(hexafluoro-2-hydroxy-2-propyl)-2,6-dimethylphenoxy]acetic acid, m.p. 118°-120° C.

EXAMPLE 5

Add ethyl 2-[4-(hexafluoro-2-methoxy-2-propyl)-2,6-dimethylphenoxy]acetate (2.6 g=6.7 mmol) to 30 ml 1.0 N NaOH. Add 20 ml methanol and reflux 3 hours. Acidify with 1.0 N HCl and extract with ether. Dry, concentrate and recrystallize the combined extracts from hexane to obtain, as a white solid, 2-[4-(hexafluoro-2-methoxy-2-propyl)-2,6-dimethylphenoxy]acetic acid, m.p. 105°-108° C.

Repetition of the above procedure utilizing ethyl 3-[4-(hexafluoro-2-hydroxy-2-propyl)-2,6-dimethylphenoxy]propionated affords 2-[4-(hexafluoro-2-methoxy-2-propyl)-2,6-dimethylphenoxy]propionic acid.

EXAMPLE 6

Combine ethyl 2-[4-(hexafluoro-2-hydroxy-2-propyl)-2,6-dimethylphenoxy]acetate (7.0 g=19 mmol) and benzylamine (12.0 g=0.11 mmol). Heat 4 hours at 110° C., allow to cool, and partition between 1.0 N HCl and ether. Dry and concentrate the ether. Recrystallize from ether-hexane and obtain, as a white solid, m.p. 142°-144° C., N-benzyl-2-[4-(hexafluoro-2-hydroxy-2-propyl)-2,6-dimethylphenoxy]acetamide.

Repetition of the above procedure utilizing dipropylamine yields N,N-dipropyl-2-[4-(hexafluoro-2-hydroxy-2-propyl)-2,6-dimethylphenoxy]acetamide.

Substitution of dibenzylamine for the benzylamine utilized in the first paragraph of this example and substantial repetition of the procedure detailed therein affords N,N-dibenzyl-2-[4-(hexafluoro-2-hydroxy-2-propyl)-2,6-dimethylphenoxy]acetamide.

EXAMPLE 7

To N-benzyl-2-[4-(hexafluoro-2-hydroxy-2-propyl)-2,6-dimethylphenoxy]acetamide (3.0 g=6.0 mmol) in 75 ml toluene add sodium bis-2-methoxyethoxy)aluminum hydride (70% solution in benzene, 8.0 g=28 mmol)

over ½ hour. Stir 16 hours, treat with 1.0 N NaOH, and extract with ethyl acetate. Dry and concentrate the organic layer. Recrystallize from ether-hexane to give 2-[4-(hexafluoro-2-hydroxy-2-propyl)-2,6-dimethylphenoxy]ethylbenzylamine, as white crystals, m.p. 117°–120° C.

Following the above procedure utilizing N,N-dimethyl-2-[4-(hexafluoro-2-hydroxy-2-propyl)-2,6-dimethylphenoxy]acetamide affords 2-[4-(hexafluoro-2-hydroxy-2-propyl)-2,6-dimethylphenoxy]ethyl-N,N-dimethylamine.

Repetition of the procedure detailed in the first paragraph using N,N-dibenzyl-2-[4-(hexafluoro-2-hydroxy-2-propyl)-2,6-dimethylphenoxy]acetamide affords 2-[4-(hexafluoro-2-hydroxy-2-propyl)-2,6-dimethylphenoxy]ethyl-N,N-dibenzylamine.

EXAMPLE 8 a. To 2,6-dimethyl-4-(hexafluoro-2-hydroxy-2-propyl)phenol (12.0 g=42 mmol) in 150 ml acetonitrile add chloroacetonitrile (3.8 g=50 mmol) and potassium carbonate (11.5 g=83 mmol). Reflux 6 hours, add more chloroacetonitrile (0.8 g=10 mmol), reflux ½ hour, and allow to cool. Filter, concentrate and partition between ether and water. Dry and concentrate the ether. Partition between 1:9 ether-hexane and 1.0 N NaOH. Acidify the aqueous layer with concentrated HCl and extract with ether. Dry and concentrate the combined ether extracts to leave a residue comprising 2-[4-(hexafluoro-2-hydroxy-2-propyl)-2,6-dimethylphenoxy]acetonitrile, together with some of the corresponding acetamide.

b. To the above oil (6.6 g=20 mmol) in 125 ml tetrahydrofuran add a solution of borane in tetrahydrofuran (120 ml, 80 mmol). Reflux 4 hours, allow to cool, add water, then 160 ml 6 N HCl and reflux 1 hour. Neutralize with Na$_2$CO$_3$ and extract with ether. Dry and concentrate the ether extracts. Boil the resultant residue with ether and filter the resulting solid to obtain 2-[4-(hexafluoro-2-hydroxy-2-propyl)-2,6-dimethylphenoxy]ethylamine, as a white solid, m.p. 167°–169° C.

EXAMPLE 9

Stir a sample of crude 2-[4-(hexafluoro-2-hydroxy-2-propyl)-2,6-dimethylphenoxy]acetonitrile, prepared as described in Example 8a, with ether for 30 minutes. Filter the solid and recrystallize from ether to obtain as a white solid, 2-[4-(hexafluoro-2-hydroxy-2-propyl)-2,6-dimethylphenoxy]acetamide, m.p. 180°–182° C.

EXAMPLE 10 a. To 4-(hexafluoro-2-hydroxy-2-propyl)-2,6-dimethylaniline (20.0 g=70 mmol), add 50 ml 4 N HCl. Reflux 1 hr., cool to 0° C., and add over 1 hour NaNO$_2$ (6.0 g=87 mmol) in 13 ml H$_2$O. After 30 min., add to a 45° C. solution of potassium ethylxanthate (14.3 g=83 mmol) in 40 ml H$_2$O. Keep at 45° C. for 30 minutes, cool, and extract with ether. Dry and concentrate. Dissolve the oil in 100 ml EtOH, add potassium hydroxide (17.5 g) and reflux 1 hour. Concentrate, then add 50 ml water and 10 ml concentrated sulfuric acid. Add 0.5 g zinc dust and steam distill. Extract the distillate with ether, dry and concentrate. Recrystallize from hexane to obtain 4-(hexafluoro-2-hydroxy-2-propyl)-2,6-dimethylthiophenol, m.p. 62°–64° C.

b. Combine the above thiophenol (6.08 g=20 mmol) with methyl bromoacetate (3.36 g=22 mmol) and potassium carbonate (5.5 g=40 mmol) in 100 ml acetonitrile. Reflux 24 hours, filter, and concentrate. Partition between ether and water, dry the ether, and concentrate. Recrystallize from hexane to obtain methyl 2-[4-(hexafluoro-2-hydroxy-2-propyl)-2,6-dimethylphenylthio]acetate, m.p. 99°–101° C.

EXAMPLE 11

Combine methyl 2-[4-(hexafluoro-2-hydroxy-2-propyl)-2,6-dimethylphenylthio]acetate with 30 ml ethanol and 5 ml 1.0 N sodium hydroxide. Reflux 4 hours, add 5 ml 1.0 N HCl, and extract with ether. Dry, concentrate and recrystallize from ether-hexane to obtain 2-[4-(hexafluoro-2-hydroxy-2-propyl)-2,6-dimethylphenylthio]acetic acid, m.p. 133°–135° C.

EXAMPLE 12

Combine 4-(2-aminohexafluoro-2-propyl)-2,6-dimethylphenol [9.0 g=31 mmol, preparation Sheppard, J. Org. Chem., 33, 3297 (1968)] with methyl bromoacetate (4.9 g=32 mmol) and potassium carbonate (4.4 g=32 mmol) in 150 ml acetonitrile. Reflux 16 hours, filter and concentrate. Partition between ether-water, and dry and concentrate the ether. Sublime at 85° C./0.1 mm pressure to obtain methyl 2-[4-(2-aminohexafluoro-2-propyl)-2,6-dimethylphenoxy)]acetate as a white solid, m.p. 93°–95° C.

EXAMPLE 13

Combine methyl 2-[4-(2-aminohexafluoro-2-propyl)-2,6-dimethylphenoxy]acetate (7.2 g=20 mmol) with 150 ml ethanol and 30 ml 1.0 N sodium hydroxide. Reflux 30 minutes and concentrate. Add 30 ml 1 N HCl and extract with ether. Dry and concentrate the ether. Sublime at 130° C./0.1 mm pressure to obtain as a white solid, 2-[4-(2-aminohexafluoro-2-propyl)-2,6-dimethylphenoxy]acetic acid, m.p. 138° C.

What is claimed is:

1. A compound of the formula

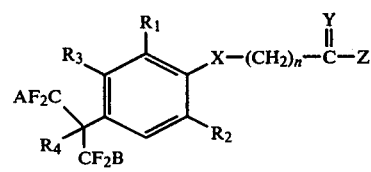

wherein A and B are independently hydrogen, chloro or fluoro;
R$_1$ is hydrogen, halo, lower alkyl or lower alkoxy;
R$_2$ is halo, lower alkyl or lower alkoxy;
R$_3$ is hydrogen or lower alkyl;
R$_4$ is hydroxy, lower alkoxy, amino, or mono- or di-lower alkylamino;
n is 1–4;
X is oxygen or S(O)$_m$ wherein m is 0–2;
Y is oxygen or (H,H); and
Z is amino, mono- or di-lower alkylamino or mono- or di-lower aralkylamino when Y is oxygen; or amino, mono- or di-lower alkylamino or lower aralkylamino when Y is (H,H); and the pharmaceutically acceptable salts thereof.

2. A compound of claim 1 wherein X and Y are both oxygen atoms.

3. A compound according to claim 2 which is 2-[4-(hexafluoro-2-hydroxy-2-propyl)-2,6-dimethylphenoxy]acetamide.

4. A compound according to claim 1 which is 2-[4-(hexafluoro-2-methoxy-2-propyl)-2,6-dimethylphenoxy]ethylamine.

5. A pharmaceutical composition adapted for the treatment of hypertension which comprises an anti-hypertensive amount of a compound according to claim 1 in admixture with a pharmaceutically acceptable carrier therefor.

6. A method for the treatment of hypertension which comprises administering to a hypertensive mammal an anti-hypertensive amount of a compound according to claim 1.

* * * * *